(12) United States Patent
Hessel et al.

(10) Patent No.: US 8,328,731 B2
(45) Date of Patent: Dec. 11, 2012

(54) METHOD AND SYSTEM FOR RECONSTRUCTING THE THREE-DIMENSIONAL SHAPE OF THE SURFACE OF AT LEAST A PORTION OF AN EAR CANAL AND/OR OF A CONCHA

(75) Inventors: Hans Hessel, Benglen (CH); Gregory Bleiker, Herrliberg (CH); Stefan Launer, Zurich (CH); Martin Roth, Staefa (CH); Bruno Knobel, Laufen (CH); Charles Findeisen, Wettingen (CH)

(73) Assignee: Phonak AG, Stafa (CH)

( * ) Notice: Subject to any disclaimer, the term of this patent is extended or adjusted under 35 U.S.C. 154(b) by 1037 days.

(21) Appl. No.: 12/160,027

(22) PCT Filed: Jan. 5, 2007

(86) PCT No.: PCT/EP2007/050126
§ 371 (c)(1),
(2), (4) Date: Jul. 3, 2008

(87) PCT Pub. No.: WO2007/045696
PCT Pub. Date: Apr. 26, 2007

(65) Prior Publication Data
US 2009/0018465 A1 Jan. 15, 2009

(30) Foreign Application Priority Data
Jan. 6, 2006 (DE) .......................... 10 2006 001 150

(51) Int. Cl.
*A61M 5/00* (2006.01)
*A61B 1/227* (2006.01)
*H04R 25/00* (2006.01)

(52) U.S. Cl. ........ 600/559; 181/129; 181/130; 181/133; 181/135; 181/136; 181/137; 381/312

(58) Field of Classification Search .................. 600/559; 181/129, 130, 133, 135, 136, 137; 381/312
See application file for complete search history.

(56) References Cited

U.S. PATENT DOCUMENTS
4,055,382 A * 10/1977 Ziekman et al. .............. 356/446
(Continued)

FOREIGN PATENT DOCUMENTS
EP 1477102 A1 11/2004
(Continued)

OTHER PUBLICATIONS
International Search Report dated Mar. 22, 2007.
(Continued)

*Primary Examiner* — Sean Dougherty
(74) *Attorney, Agent, or Firm* — Pearne & Gordon LLP

(57) ABSTRACT

The method for reconstructing the three-dimensional shape of the surface (14) of at least a portion of an ear canal (18) and/or of a concha comprises—for each of a multitude of points (12) on said surface (14)—the step of using a chromatic coded distance measurement technique for determining a distance value (40) representative of a distance to said point (12); and further comprises the step of reconstructing said three-dimensional shape based on said multitude of distance values (40). The system for reconstructing the three-dimensional shape of the surface (14) of at least a portion of an ear canal (18) and/or of a concha, comprises a distance measurement unit for determining—by means of a chromatic coded distance measurement technique and for each of a multitude of points (12) on said surface (14)—a distance value (40) representative of a distance to said point; and a reconstructing unit (50) operationally connected to said distance measurement unit for reconstructing said three-dimensional shape based on said multitude of distance values (40).

16 Claims, 4 Drawing Sheets

U.S. PATENT DOCUMENTS

| | | | | |
|---|---|---|---|---|
| 4,355,904 | A * | 10/1982 | Balasubramanian | 356/608 |
| 4,585,349 | A * | 4/1986 | Gross et al. | 356/624 |
| 4,791,293 | A * | 12/1988 | Barriere | 250/302 |
| 4,963,018 | A * | 10/1990 | West | 356/3.05 |
| 4,967,092 | A * | 10/1990 | Fraignier et al. | 250/559.07 |
| 5,044,373 | A * | 9/1991 | Northeved et al. | 600/559 |
| 5,165,063 | A | 11/1992 | Strater | |
| 5,716,324 | A * | 2/1998 | Toida | 600/160 |
| 5,785,651 | A * | 7/1998 | Kuhn et al. | 600/310 |
| 5,895,927 | A * | 4/1999 | Brown | 250/559.19 |
| 6,069,698 | A * | 5/2000 | Ozawa et al. | 356/511 |
| 6,208,465 | B1 * | 3/2001 | Schaham | 359/558 |
| 6,263,234 | B1 * | 7/2001 | Engelhardt et al. | 600/476 |
| 6,327,041 | B1 * | 12/2001 | Guern | 356/601 |
| 6,462,815 | B1 * | 10/2002 | Drabarek et al. | 356/241.1 |
| 6,470,124 | B1 * | 10/2002 | Le Gargasson et al. | 385/117 |
| 6,633,378 | B2 * | 10/2003 | Doyle, Jr. | 356/241.1 |
| 6,753,966 | B2 * | 6/2004 | Von Rosenberg | 356/432 |
| 6,781,699 | B2 * | 8/2004 | Dunn et al. | 356/511 |
| 6,937,348 | B2 * | 8/2005 | Geng | 356/603 |
| 7,038,793 | B2 * | 5/2006 | Schick | 356/614 |
| 7,164,476 | B2 * | 1/2007 | Shima et al. | 356/241.1 |
| 7,554,731 | B2 * | 6/2009 | Dowski, Jr. | 359/558 |
| 7,554,732 | B2 * | 6/2009 | Dowski, Jr. | 359/558 |
| 7,625,335 | B2 * | 12/2009 | Deichmann et al. | 600/117 |
| 7,660,426 | B2 * | 2/2010 | Hannibal et al. | 381/312 |
| 7,949,385 | B2 * | 5/2011 | Khamene et al. | 600/416 |
| 7,961,981 | B2 * | 6/2011 | Berg | 382/286 |
| 2003/0021434 | A1 * | 1/2003 | Hessel et al. | 381/312 |
| 2003/0164952 | A1 * | 9/2003 | Deichmann et al. | 356/603 |
| 2003/0223083 | A1 | 12/2003 | Geng | |
| 2004/0107080 | A1 * | 6/2004 | Deichmann et al. | 703/6 |
| 2004/0109170 | A1 * | 6/2004 | Schick | 356/614 |
| 2005/0068544 | A1 * | 3/2005 | Doemens et al. | 356/601 |
| 2005/0088435 | A1 * | 4/2005 | Geng | 345/419 |
| 2006/0276709 | A1 * | 12/2006 | Khamene et al. | 600/416 |
| 2007/0057942 | A1 * | 3/2007 | Unal et al. | 345/419 |
| 2007/0153296 | A1 * | 7/2007 | Schick | 356/609 |
| 2010/0149550 | A1 * | 6/2010 | Diefenbacher et al. | 356/601 |
| 2011/0130645 | A9 * | 6/2011 | Khamene et al. | 600/416 |

FOREIGN PATENT DOCUMENTS

| | | |
|---|---|---|
| WO | 02/16867 A1 | 2/2002 |
| WO | 0216567 A2 | 2/2002 |
| WO | 0221894 A2 | 3/2002 |
| WO | 02/091920 A1 | 11/2002 |

OTHER PUBLICATIONS

Written Opinion for PCT/EP2007/050126 date May 4, 2007.

* cited by examiner

METHOD AND SYSTEM FOR RECONSTRUCTING THE THREE-DIMENSIONAL SHAPE OF THE SURFACE OF AT LEAST A PORTION OF AN EAR CANAL AND/OR OF A CONCHA

TECHNICAL FIELD

The invention relates to the field of measuring parts of the human body, more precisely of the human ear, and to the field of manufacturing hearing devices. It relates to methods and apparatuses according to the opening clause of the claims.

Under a hearing device, a device is understood, which is worn in or adjacent to an individual's ear with the object to improve the individual's acoustical perception. Such improvement may also be barring acoustic signals from being perceived in the sense of hearing protection for the individual. If the hearing device is tailored so as to improve the perception of a hearing impaired individual towards hearing perception of a "standard" individual, then we speak of a hearing-aid device. With respect to the application area, a hearing device may be applied behind the ear, in the ear, completely in the ear canal or may be implanted.

BACKGROUND OF THE INVENTION

With respect to their outer shape, most of today's hearing devices are in full or in part individually adapted to the shape of the ear of the individual wearing the hearing device, in particular to the shape of the ear canal and/or of the concha. BTE (behind the ear) hearing device comprise an ear mold, which is individualized, and in case of ITE (in the ear) hearing device, in particular ITC (in the canal) and CIC (completely in the canal) hearing devices, at least a portion of the shell or housing of the hearing device is individualized. For a proper function of a hearing device and for a comfortable wearing experience of the hearing device user, it is necessary to precisely reproduce the shape of the ear canal and/or concha, typically within fractions of a millimeter.

For this individualization, usually ear impressions in silicone are made by applying viscous silicone to the outer ear and the ear canal. After curing of the silicone and removal from the ear, the shape is three-dimensionally scanned for building a shell on basis of so-obtained scanning data, or it is used for forming a negative, by means of which a (positive) shell is then created.

Taking such silicone impressions is a very delicate process, as it requires special skills and depends on various parameters.

Therefore, an improved reproducibility is desirable, as well as a simplification of process steps to be carried out by persons involved.

Several non-contact measuring techniques have been described in the art.

WO 02/21894 A2 describes a non-contact optical method for reconstructing the shape of the inner surface of an ear canal, in which video signals from inside the ear canal are recorded and analyzed. This analysis yields position data of said inner surface, based on which hearing device shells can be manufactured.

Another optical non-contact measurement method for ear canals is disclosed in WO 02/16867 A1. In this case, structured light is projected onto the surface to be measured. The so-obtained pattern is imaged by a camera and analyzed, so as to yield the desired three-dimensional shape.

Yet another optical non-contact measurement method for ear canals is disclosed in WO 02/091920 A1. In this case, light is directed at the inner ear canal surface to be measured. The reflected light is detected and analyzed with respect to its light path (angle and/or position). By means of geometrical methods (triangulation), the distance of the probe to the ear canal surface can be obtained.

Due to the relatively low absorption of light in the human skin (epidermis, dermis), a halo of considerable intensity and size is created near incident light (due to volume scattering in the epidermis, dermis), so that the above-described non-contact optical methods tend to yield results of insufficient accuracy, at least unless the skin is specifically prepared, e.g., by covering it with talcum powder.

It is desirable to create an alternative method and system for reconstructing the three-dimensional shape of the surface of at least a portion of an ear canal and/or of a concha, in particular a method and system providing for an increased accuracy and/or reproducibility.

SUMMARY OF THE INVENTION

Therefore, one object of the invention is to create a method and a system for reconstructing the three-dimensional shape of the surface of at least a portion of an ear canal and/or of a concha that do not have the disadvantages mentioned above. In addition, a corresponding method for manufacturing a hearing device and a corresponding method for reconstructing the three-dimensional shape of the surface of at least a portion of the ear canal and/or of the concha of an individual's left ear and of said individual's right ear shall be provided.

Another object of the invention is to provide for an increased reproducibility.

Another object of the invention is to provide for an increased accuracy.

Another object of the invention is to provide for a simplification of steps to be done manually.

Further objects emerge from the description and embodiments below.

At least one of these objects is at least partially achieved by apparatuses and methods according to the patent claims.

The method for reconstructing the three-dimensional shape of the surface of at least a portion of an ear canal and/or of a concha comprises—for each of a multitude of points on said surface—the step of using a chromatic coded distance measurement technique for determining a distance value representative of a distance to said point, and further comprises the step of reconstructing said three-dimensional shape based on said multitude of distance values.

Through this, an increased accuracy can be achieved.

A great advantage of chromatic coded distance measurement techniques is that light that is analyzed for obtaining said distance values originates mainly from an illuminated spot at the surface to be measured and from a small volume just beneath. Light originating from elsewhere is not analyzed and therefore does not contribute to the distance measurement.

Another advantage of chromatic coded distance measurement techniques ist that they yield absolute distances.

The chromatic coded principle is known in the art. It is disclosed, e.g., in the homepage www.precitec.de of Precitec Optronik GmbH, Rodgau, Germany, in particular at http://www.precitec.de/chrocodile/enxml/products/contactless-measuringsensor_chrocodile_measuringprinciple.html
and at
http://www.precitec.de/chrocodile/images/products/large/chromatisch.jpg,
and also in the homepage www.stilsa.com of the company STIL, Aix-en-Provence, Francey, in particular at http://www.stilsa.com/EN/sommaire/lprin.htm.

The chromatic coded distance measurement techniques, also known as chromatic confocal measurement techniques, base upon the fact that light focused by means of a chromatic optical system, i.e., an optical system with high chromatic aberration and strong dispersion, has distinctly different focal lengths for light of distinctly different wavelengths. This allows to encode distances in wavelengths.

In the systems disclosed in said homepages www.precitec.de and www.stilsa.com, light is focused along the optical axis of system optics, and areal measurements or measurements of surfaces are accomplished by mechanically displacing said system optics relative to the area or surface to be measured in a plane perpendicular to said optical axis.

Said distance to said point in the above-described method according to the invention may, e.g., be a distance from a reference point to said point and/or a distance along an optical path, in particular a distance along a light beam used for obtaining said distance value.

In one embodiment, the method comprises the steps of
a) illuminating said multitude of points by means of polychromatic light emitted from a probe located near or in said ear canal and/or concha;
b) collecting light reemitted from said surface upon said illumination;
c) analyzing said collected light with respect to its color;
d) obtaining said multitude of distance values from said analyzing.

Preferably, said collecting (step b)) is accomplished by means of said probe.

Said illuminating said multitude of points (step a)) may be accomplished one by one (serially, one point at a time) or in a parallel manner, illuminating several points at the same time. In the latter case, preferably also steps b) and c) are also carried out in a parallel manner.

In one embodiment, the method comprises the step of moving said probe relatively to said canal and/or concha while carrying out steps a) and b).

Preferably, said probe is moved manually. The probe may be a hand-held probe, which is moved to and then near or within said ear canal and/or concha.

In one embodiment of the method, said probe comprises a chromatic optical system, and said polychromatic light emitted from said probe forms at least one focused beam towards one of said multitude of points, and said method comprises the step of choosing the position and/or orientation of said probe such that said focused beam is focused at said point for at least one wavelength of said polychromatic light, while the beam is focused before and/or after said point for other wavelengths of said polychromatic light.

Preferably, said focused beam is focused at said point for one wavelength of said polychromatic light.

The distance range within which measurements can take place by means of a chromatic coded distance measurement technique depends on the chromatic optical system, in particular its aberration or dispersion, and on the wavelength range of the light employed. Accordingly, it is advisable to locate the probe such that the surface to be measured is within said distance range within which measurements can take place.

Said polychromatic light emitted from said probe can be one focused beam to one point to be measured or can be several focused beams, each to a different point to be measured.

In one embodiment, said chromatic optical system comprises entrance optics and chromatic optics having an optical axis, said method comprising the steps of k) feeding polychromatic light emitted from a light source to said entrance optics;
l) forming at least one light beam in said entrance optics;
m) feeding said at least one light beam from said entrance optics to said chromatic optics
  at a distance from said optical axis, and
  at an azimuthal and a polar angle with respect to said optical axis,
    wherein at least one of said distance, said azimuthal angle and said polar angle is selectable by means of said entrance optics;
n) forming said focused beam by means of said chromatic optics.

Said light source is polychromatic light source, typically a white-light source. Said light source can be optionally comprised in said chromatic optical system. Preferably, said light source emits parallel light.

Said entrance optics may be achromatic. It receives light from said light source and feeds it to said chromatic optical system. By means of said entrance optics, it can be determined, which point or points on the surface will be illuminated, i.e., the entrance optics allows to select different points on said surface. This is preferably accomplished by forming one or several beams of polychromatic light, each arriving at said chromatic optics at a certain selectable distance to said optical axis of said chromatic optics and/or at a certain selectable polar angle and/or at a certain selectable azimuthal angle. One, two or all three of said magnitudes determine the direction of light emitted from the probe (at given chromatic optics), and thus determine the point to be measured.

Typically, said entrance optics and/or a housing, which houses the entrance optics, is of oblong shape. It may be straight or curved and/or angled.

In one embodiment, the method comprises the steps of
p) carrying out step b) by means of said chromatic optics;
q) feeding said collected light from said chromatic optics to said entrance optics;
r) coupling said collected light out of said entrance optics for carrying out step c).

Preferably, only light travelling the same light path from the entrance optics through the chromatic optics and to said at least one point as travelling back from said point through said chromatic optics and to said entrance optics will be analyzed with respect to its color (step c)).

Step r) may be accomplished, e.g., by means of a beam splitter.

In one embodiment, said chromatic optical system has a field of view, which comprises—continuously or quasi-continuously—substantially 360° in azimuthal angle with respect to said optical axis and which comprises a continuous or quasi-continuous range of polar angles with respect to said optical axis.

The field of view is defined by the angular range of the directions into which said polychromatic light can be emitted from said probe, in particular from said chromatic optics.

Preferably, said field of view is substantially rotationally symmetric about said optical axis.

Said polar angle range preferably spans at least 20°, preferably at least 60° or at least 90° or at least 110°. Preferably, the major part of said field of view is off-axis. Although usually not preferred, it is possible to exclude a polar angle range from said field of view, which comprises 0°, i.e., on-axis emission. This could be useful if the on-axis direction (polar angle 0°) and possibly also neighboring directions are used for different purposes, e.g., for a collision-prevention system.

In one embodiment, said field of view substantially defines a closed-loop stripe around the probe. This renders rotating the probe about the optical axis superfluous.

In one embodiment, step a) is carried out simultaneously for several of said points. Measuring in such a parallel manner can save considerable amounts of measuring time. But the analysis (step c)) has to be more advanced; e.g., a one- or two-dimensional array of color sensors or spectrometers should be employed, e.g., a CMOS sensor as used in today's digital color photographic cameras.

For reconstructing the shape in sufficiently high resolution, it will typically be necessary to proceed in a scanning manner. I.e., if N distances (each to one point) can be measured simultaneously ($N \geq 1$), many times (of the order of 100 to 10000) such N simultaneous distance measurements will be accomplished after each other, fully or mostly for different points on the surface to be measured.

In one embodiment, the method comprises the step of
u) tracking at least one of
  the position in space and/or the orientation in space of said probe;
  the position in space and/or the orientation in space of said ear canal and/or concha;
  the relative position and/or mutual orientation of said probe and said ear canal and/or concha;
  and generating corresponding tracking data; and
v) using said tracking data in said reconstructing said three-dimensional shape.

Since it is not practicable or even impossible to fix the relative position and relative orientation of the probe and the ear to be measured, it is advisable to keep track of these. This allows to determine said three-dimensional shape of said surface with high precision, even if the individual's head is moving while taking data and/or when the probe is hand-held.

Such a tracking even allows to relate measurements taken at one ear of an individual to measurements taken at the other ear of said individual. I.e., the relative position (and mutual orientation) of the shape determined at the one ear and the shape determined at the other ear can be related to a common coordinate system. This can be very advantageous, e.g., when hearing devices to be manufactured on basis of these reconstructed shapes comprise a beam former (beam formers are well known in the field of hearing devices).

Preferably, each distance value is related to tracking data taken at the same time. Of course, interpolation and also extrapolation of tracking data is possible, too.

In one embodiment, the method comprises the step of carrying out step u) by means of an optical tracking system. Suitable optical tracking systems are commercially available.

In one embodiment, the method comprises the step of carrying out step u) by means of at least one tracing element attached to said probe and at least one tracing element attached to the head of an individual to which said ear canal and/or concha belong.

In one embodiment, the method comprises the steps of
  monitoring the distance between said probe and said ear canal; and
  generating an alert if said distance is below a prescribable threshold distance or if said distance is assumed to drop below a prescribable threshold distance.

This allows to prevent unwanted collisions of the probe with a part of the individual's ear, in particular with the tympanic membrane. Such a collision-prevention system is particularly important in case of a hand-held probe.

This monitoring may be accomplished an optical technique.

The monitoring may take place continuously or quasi-continuously, e.g., intermittent with distance measurements for determining said shape.

Since the tympanic membrane is particularly sensitive, it can be advantageous to monitor said distance substantially parallel to said optical axis of said chromatic optics.

In one embodiment, the method comprises the step of qualitatively visually inspecting said ear canal and/or said concha by means of an endoscope.

Such a visualization can considerably ease the handling of the probe.

Preferably, said endoscope is integrated in or attached to said probe.

The method for reconstructing the three-dimensional shape of the surface of at least a portion of the ear canal and/or of the concha of an individual's left ear and of said individual's right ear comprises carrying out a method with said tracking as described above, for said individual's left and right ears.

Preferably, said method comprises the step of relating said tracking data obtained for said left ear and said tracking data obtained for said right ear to a common coordinate system.

The system for reconstructing the three-dimensional shape of the surface of at least a portion of an ear canal and/or of a concha comprises
  a distance measurement unit for determining—by means of a chromatic coded distance measurement technique and for each of a multitude of points on said surface—a distance value representative of a distance to said point; and
  a reconstructing unit operationally connected to said distance measurement unit for reconstructing said three-dimensional shape based on said multitude of distance values.

In one embodiment, said distance measurement unit comprises
  a probe to be moved close to and/or into said ear canal and/or concha for emitting polychromatic light towards said ear canal and/or concha for illuminating said multitude of points and for collecting light reemitted from said surface upon said illumination;
  a color analyzing unit operationally connected to said probe for analyzing said collected light with respect to its color;
  an evaluation unit operationally connected to said color analyzing unit for obtaining said multitude of distance values from said analyzing.

Suitable color analyzing units comprise, e.g., at least one spectrometer, at least one spectrum analyzer, at least one color sensor.

Said probe is preferably a hand-held probe.

The advantages of the systems correspond to the advantages of corresponding methods. Only some of the embodiments of the system will be discussed in the following.

In one embodiment, said probe comprises a chromatic optical system for emitting said polychromatic light towards said ear canal and/or concha in form of at least one focused beam having distinctly different focal lengths for distinctly different wavelengths of said polychromatic light.

In one embodiment, said distance measurement unit comprises a polychromatic light source, and wherein said chromatic optical system comprises entrance optics for receiving polychromatic light emitted from said polychromatic light source, and chromatic optics having an optical axis, for forming said at least one focused beam, wherein said entrance optics is capable of forming at least one light beam and of feeding said at least one light beam to said chromatic optics at a distance from said optical axis, and
at an azimuthal and a polar angle with respect to said optical axis,
wherein at least one of said distance, said azimuthal angle and said polar angle is selectable by means of said entrance optics.

In one embodiment, said chromatic optical system can be detachable from said probe and/or said entrance optics and/or said chromatic optics can be detachable from said probe. This allows to exchange these parts when necessary, e.g., if once, the ear canal of a young child shall be investigated and another time, an adult's ear canal being considerably larger than the child's ear canal shall be investigated. Preferably, in this case the detachable part comprises code information, which can be transmitted (e.g., electronically and automatically) to another part of the system, in particular to said evaluation unit, so as to ensure a correct determination of said distance values.

In one embodiment, said entrance optics comprises, for said selecting, at least one mirror rotatable about at least two axes, or at least two mirrors, each rotatable about at least one axis, which two axes are not parallel to each other. Said entrance optics may comprise an array of such mirrors or such pairs of mirrors, e.g., in form of a MEMS (micro electromechanical systems), wherein said mirrors are continuosly or quasi-continuously rotatable.

In one embodiment, said entrance optics comprises an array of micro-mirrors for said selecting. Examples for such arrays are MEMS (micro electro-mechanical systems), e.g., a DMD (Digital Mirror Device). Such micro-mirros may possibly have only one, two or three (typically two) defined positions.

The latter two embodiments are examples of how to accomplish said selection of at least one of said distance, said azimuthal angle and said polar angle.

In one embodiment, said entrance optics comprises a beam splitter for coupling out said collected light to said color analyzing unit. Said beam splitter may be embodied, e.g., as a semi-transparent mirror.

In one embodiment, said probe is capable of emitting polychromatic light towards said ear canal and/or concha by simultaneously emitting several focused beams having distinctly different focal lengths for distinctly different wavelengths of said polychromatic light.

Preferably, said emission takes place from said chromatic optics. Preferably, said several beams are selected by means of said entrance optics.

The method for manufacturing a hearing device comprises the steps of
reconstructing the three-dimensional shape of the surface of at least a portion of an ear canal and/or said concha according to one of the above-mentioned method claims; and
manufacturing at least a part of said hearing device, based on said reconstruction.

That part of said hearing device can, in particular, be a shell or casing of said hearing device or a part thereof, or an ear mold.

Further preferred embodiments and advantages emerge from the dependent claims and the figures.

Considered under a broadened and more general point of view, the invention does not have to confine to reconstructing shapes of surfaces of ear canals and/or conchas, but may relate to the reconstruction of shapes of surfaces of any kind of hollow or cavity or to the measurement of the three-dimensional topology of hollows and area regions about their entrances. Examples for such hollows are tapped blind holes and internal screw threads.

BRIEF DESCRIPTION OF THE DRAWINGS

Below, the invention is described in more detail by means of examples and the included drawings. The figures show.

The reference symbols used in the figures and their meaning are summarized in the list of reference symbols. The described embodiments are meant as examples and shall not confine the invention.

DETAILED DESCRIPTION OF THE INVENTION

Figure 1:
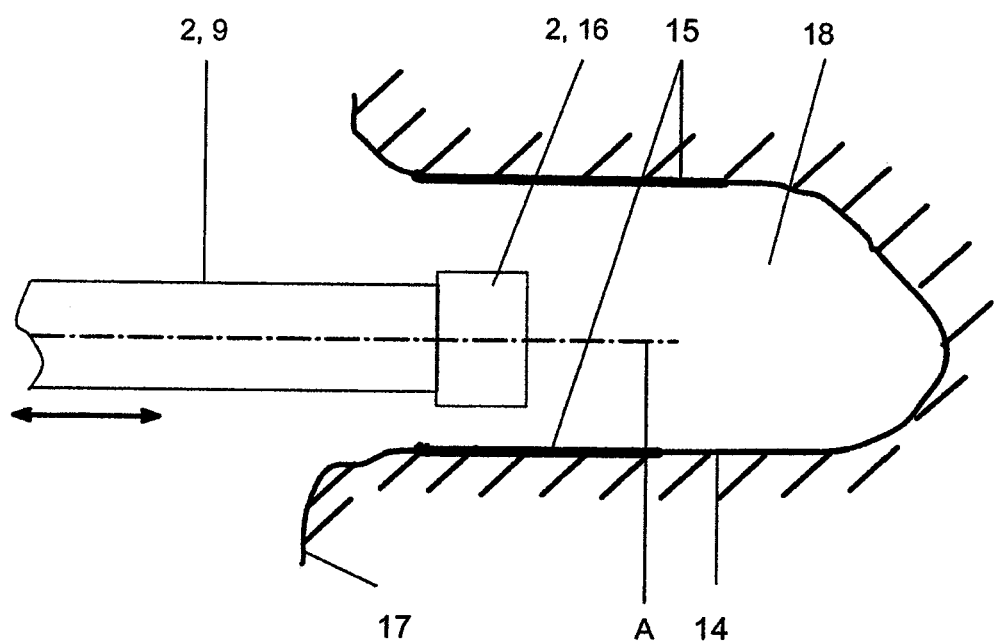
FIG. 1 a schematic illustration of a measuring procedure.

FIG. 1 shows a schematic illustration of a measuring procedure. A probe 2 has been moved into a hollow 18 to be investigated, which is an ear canal 18 of an individual, shown in cross-section. The surface (inner surface) of the ear canal 18 is labelled 14, the surface of the entrance of the ear canal, which is the surface of the concha, is labelled 17.

The probe 2 comprises a chromatic optical system, which is not shown in FIG. 1 and comprises entrance optics and chromatic optics having an optical axis A. For measuring a distance to a point of said surface 14, a chromatic coded distance measurement technique is used. Accordingly, light is emitted from probe 2, and the light thereupon reemitted from the surface 14 is analyzed with respect to its color, wherefrom said distance can be determined. Said distance is usually a distance from a reference point at said probe 2 to said point at said surface 14.

Said light emitted from said probe 2 is emitted from the front part of the probe, formed by a housing 16 of said chromatic optics. Measurements can take place only within the field of view of said chromatic optical system, i.e., within the angular range of the directions into which said light can be emitted from said probe 2. That part of said surface 14, which lies within said field of view, is labelled 15 (thick line in FIG. 1).

Said chromatic optics preferably is a fish-eye-type chromatic objective and covers, as indicated in FIG. 1, a large part of solid angle sideways of the probe 2. Nevertheless, for measuring a sufficiently large portion of ear canal 18, it will usually be necessary to move probe 2 within the ear canal 18, as indicated by the arrow in FIG. 1.

Probe 2 is preferably of generally oblong shape and comprises a housing 9 for said entrance optics, which is attached to or comprises said housing 16 of said chromatic optics, and which usually is of generally oblong shape.

If probe 2 is moved out of ear canal 18, it is also possible to investigate parts of surface 17, i.e., to investigate the concha. If this is intended, a field of view comprising angles of light emission from said chromatic optics which are closer to axis A would be of advantage. Otherwise, tilting probe 2 could allow to investige the concha.

Figure 2:
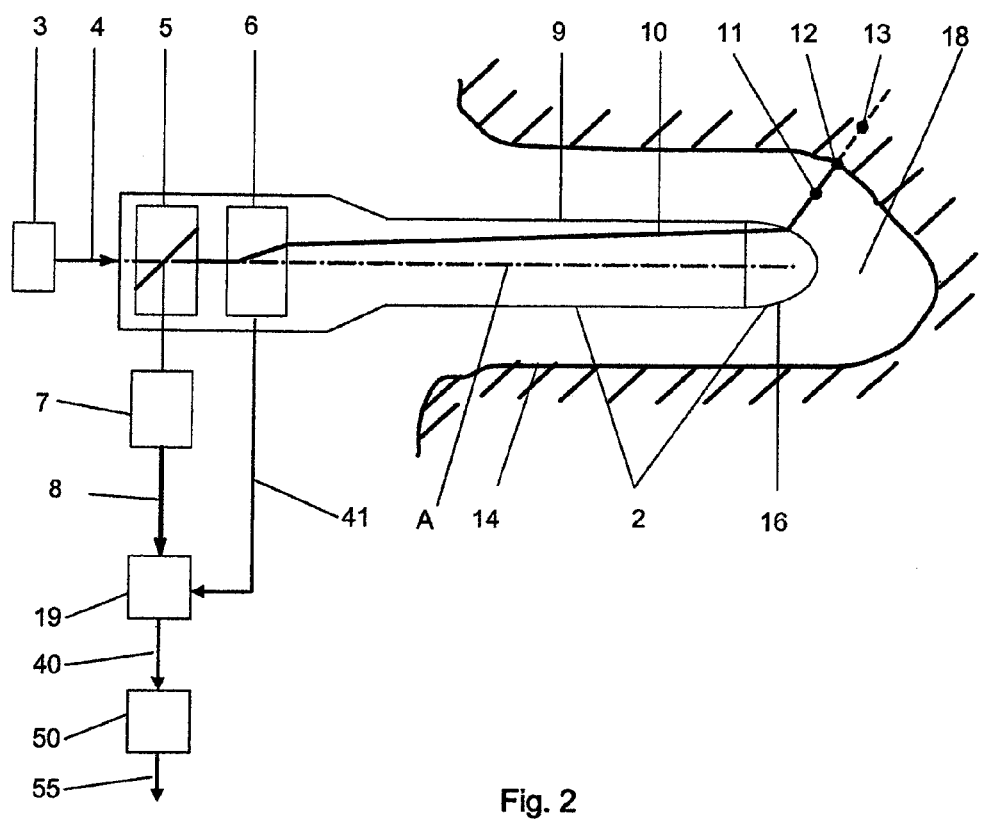
FIG. 2 schematically a measuring system.

FIG. 2 shows schematically a measuring system of the type shown in FIG. 1. The system comprises a light source 3, a beam splitter 5, a light deflecting unit 6, entrance optics in a housing 9, chromatic optics in a housing 16, a color analyzing unit 7, an evaluation unit 19, and a reconstruction unit 50. Entrance optics and chromatic optics are comprised in a chromatic optical system of the measuring system. Probe 2 of the system is inserted into an ear canal 18 to be measured having an inner surface 14 (shown in cross-section).

Light source 3 generates polychromatic, preferably parallel light 4. Said light 4 traverses beam splitter 5 and enters light deflecting unit 6. Light deflecting unit 6 can be, e.g., a mirror arrangement, e.g., a MEMS like a DMD or one mirror continuously or quasi-continuously rotatable about at least two axes or two mirrors continuously or quasi-continuously rotatable about at least one axis each, which axes are preferably perpendicular to each other.

By means of light deflecting unit 6, a light beam can be fed into said chromatic optics under a prescribable polar and/or azimuthal angle (with respect to axis A) and/or a prescribable distance from axis A. It is, in particular with MEMS in a light deflecting unit 6, possible to simultaneously generate several of such light beams. In the following description, the case of only one such beam, labelled 10, will be discussed for reasons of simplicity.

In said chromatic optics, said light beam 10 will be emitted towards a point 12 of surface 14 lying within the field of view of said chromatic optical system. The direction of this emission is determined by said parameters selected in said entrance optics (polar angle, azimuthal angle, distance to axis A). More precisely, the light beam will be focused onto said point 12 of surface 14, but point 12 will be in-focus only for one wavelength of the polychromatic light beam, e.g., for green light. The focused beam will be in-focus before or after surface 14 for light of different wavelength, e.g., for blue light at the point labelled 11 and for red light at the point labelled 13. This is due to the strong chromatic aberration of said chromatic optics. Said chromatic optics typically comprises several lenses made of material of great dispersion, and, in addition, one or more apertures.

The light emitted from surface 14 thereupon is collected by probe 2. More particularly, the light travels back through said chromatic optics and said entrance optics the same way as it came, only that it is reflected into color analyzing unit 7 by means of beam splitter 5.

Color analyzing unit 7 may be a spectrometer and outputs data 8 related to the color, i.e., spectral contents, of the back-travelled light.

These data 8 are fed to evaluation unit 19, which, in addition, receives data 41 from light deflecting unit 6 related to the location of the currently investigated point 12 (with respect to probe 2). These data 8 and 41 are evaluated in evaluation unit 19, and data 40 related to location of point 12 and distance to point 12 are obtained. In evaluation unit 19, the measured spectrum (or, more general, information obtained about the color) is related to the absolute focal length.

If probe 2 and ear canal 18 are perfectly still (at least with respect to each other), it is possible to reconstruct the shape of ear canal 18 from such data 40 taken for a multitude of points of surface 14. This can be accomplished by serially selecting many different points of surface 14 by means of the entrance optics or, more particular, by means of light deflecting unit 6. Of course, only such points on surface 14 can be investigated, which lie within the field of view of said chromatic optical system and which additionally lie within the accessible distance range of said chromatic optical system. The accessible distance range is mainly determined by the wavelength range of the polychromatic light and by the chromatic aberration of said chromatic optics, which is readily understood looking at points 11,12,13 in FIG. 2.

Data 40 are fed to reconstruction unit 50 for reconstructing the three-dimensional shape of the investigated part of surface 14 therefrom and outputting corresponding reconstruction data 55 for further use.

Since it is desirable to hold probe 2 manually and even move it manually, and since the individual to whom the ear canal belongs will usually not be able to keep his head sufficiently still during data gathering, an extension of the measuring system taking these problems into account is desirable to have.

Figure 3:
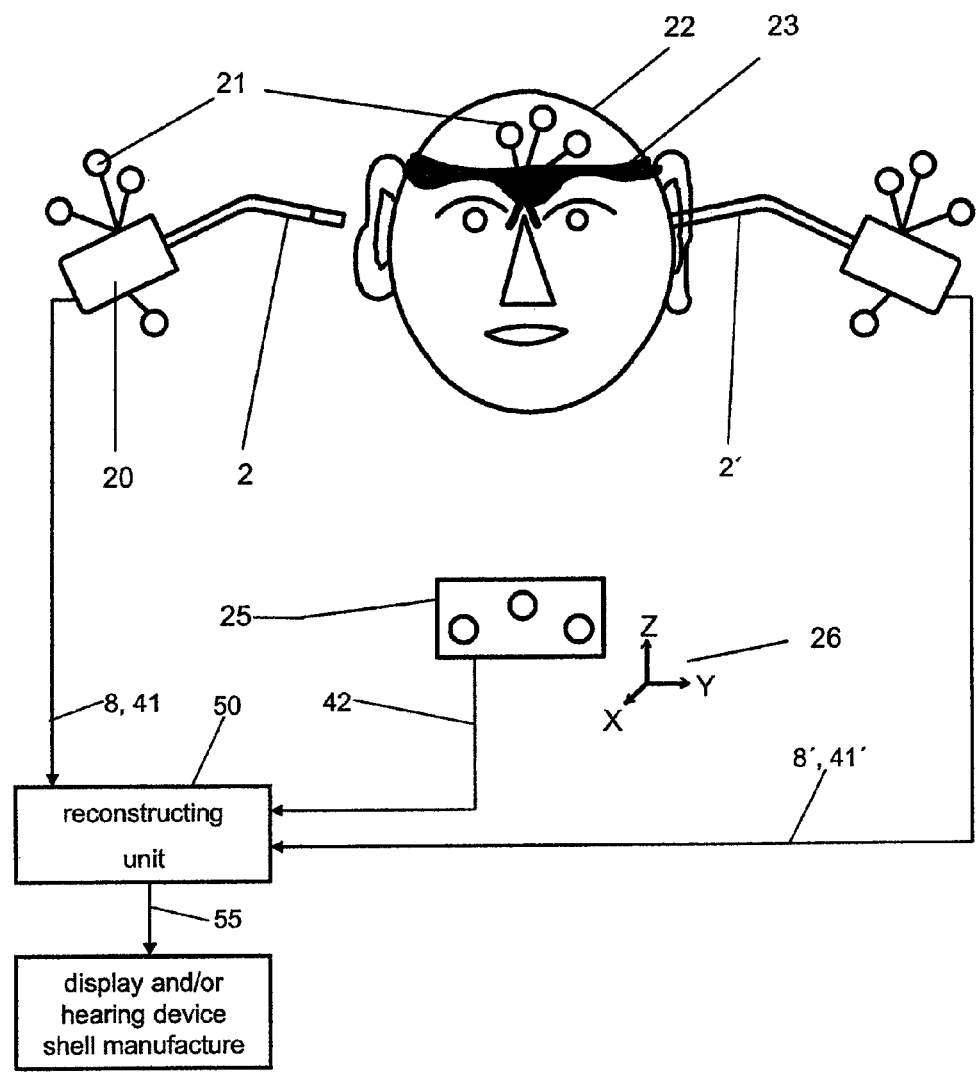
FIG. 3 a schematic illustration of a measuring procedure and of a measuring system.

FIG. 3 shows a schematic illustration of a measuring procedure and of a measuring system taking care of the above-mentioned problem. In addition, the embodiment of FIG. 3 allows to relate measurements made at the right ear of an individual and measurements made at the left ear of that individual to a common coordinate system 26.

FIG. 3 shows an individual's head 22, to which at least one tracing element 21, e.g., at least three tracing elements 21 are attached, e.g., using a tracing element carrier 23 attached to the individual's head 22. The tracing elements 21 are parts of a tracking system, which not only allows to track the position in space and orientation in space of the individual's head 22, but also the position in space and orientation in space of a probe 2 (said probe 2 can be a probe as discussed in FIGS. 1 and 2). For this purpose, at least one further tracing element 21, e.g., at least three tracing elements 21 are attached to probe 2, e.g., to a handle 20 of probe 2. In addition, the tracking system comprises a tracking unit 25, which is operationally connected to said tracing elements 21, and which preferably is fixed in space, and which generates tracking data 42, which indicate the current relative position and current relative orientation of probe 2 and head 22, wherein the position and orientation of head 22 is used as indicator for the position and orientation of the individual's ear canal and/or concha. A tracing element can be or comprise what is referred to as a "marker" or what is referred to as a "locator" in the field of tracking systems.

Using a tracking system simplifies the reconstruction of the investigated surface topology and will increase the achievable accuracy and/or reproducibility.

Furthermore, the possibility of moving and rotating the probe 2 with respect to the surface 14 has the advantage, that nominally the same point can be measured several times, but from different probe locations and, accordingly, under different illumination angles. This can be helpful for detecting obstacles and dirt. During calculating the topology, such obstacles and dirt can be considered.

Suitable tracking systems, in particular optical tracking systems, are commercially available, e.g., from the companies Northern Digital Inc. (www.ndigital.com) or Atracsys LLC (www.atracsys.com). In case of optical tracking systems, said tracing elements 21 can comprise or be, e.g., active light points such as LEDs or passive light points such as retro-reflective spheres.

From probe 2, data 8 from a color analyzing unit 7 (cf. FIG. 2) of the probe 2, related to the color of the light reemitted from the surface to be measured, and data 41 from a light deflecting unit 6 (cf. FIG. 2) of probe 2, related to the location of a point to be measured relative to the probe 2, are fed to a reconstructing unit 50, which, in addition, receives said tracking data 42 from tracking unit 25.

On basis of all these data, reconstructing unit 50 can reconstruct the three-dimensional shape of at least a portion of the individual's ear canal 18 and/or concha, even if the probe is hand-held and (slowly) moved with respect to the individual's head 22, wherein a fixation of head 22 is not necessary. Reconstructing unit 50 generates reconstruction data, which can be used for displaying them and visualizing the investigated surface, which can be helpful during data gathering, and/or for manufacturing a part of a hearing device, which is to be worn in the individual's ear canal and/or concha, e.g., a shell or casing of a hearing device or an ear mold or a part thereof.

With 2', another probe is labelled by means of which the second ear of the individual can be examined at the same time as the first ear. In an alternative interpretation of FIG. 3, probes 2 and 2' are one identical probe, but at different points in time. Nevertheless, in both cases data 8 and 8' and data 41 and 41' are generated and fed to reconstructing unit 50, which allows to reconstruct both ear canals in the same coordinate system 26.

In another possible embodiment, which is not shown in a Figure, a tracking system is used, which comprises sensors which measure linear accelerations and angular rates preferably about all three axes and preferably for the probe and/or for the surface to be measured (inner surface of the ear canal). Such sensors can be integrated in the probe and attached to the individual's head, respectively. The sensor data allow to quantify any movements of the probe and/or of the person's head, preferably both, in which case the relative position and orientation of probe and surface can be determined. An appropriate tracking unit not only allows to determine the current situation, but allows also to predict the situation in the next future, which can be advantageous in conjunction with collision-prevention systems integrated in the measuring system.

Figure 4:
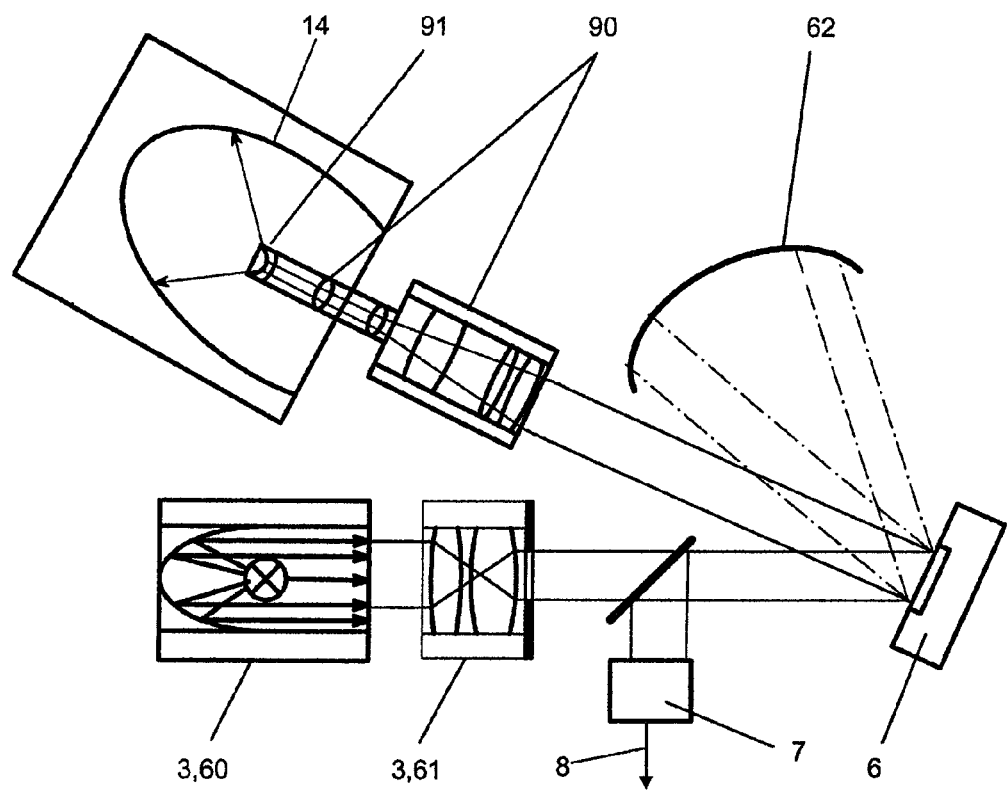
FIG. 4 schematically a portion of a measuring system, emphasizing optical components.

FIG. 4 schematically shows a portion of measuring system, emphasizing optical components. The measuring system can be one as discussed in conjunction with FIG. 2 or FIG. 3, and it will be described based thereon. The light source 3 comprises a light generator in a parabolic mirror 60 and a beam expander 61. It would also be possible to use a light generator followed by a condenser. The beam splitter is a semi-transparent mirror.

The light deflecting unit is a DMD, i.e., an array of a multitude of micro-mirrors, which can be switched between at least two positions. Controlling the DMD allows to select one or several partial beams from the parallel light bundle impinging on it. The selected partial light beams are fed to the chromatic optics. The other partial light beams (indicated by dash-dotted lines) are trapped in a light trap 62. The entrance optics may comprise further optical elements like lenses and apertures.

The chromatic optics 90 comprises several lenses and typically also at least one aperture.

Near the end 91 of the chromatic optics, at least one focused beam with wavelength-dependent focal length leaves the probe, and at the same place 91, the reemitted light is collected again. In the cross-sectional view of FIG. 4, two such beams are drawn. The DMD may be used in such a way that simultaneously several beams are emitted from the probe, e.g., all having substantially the same polar angle but different azimuthal angles. In this case, it is advantageous to have a corresponding number of simultaneously available spectrometers or color sensors in color analyzing unit 7. For investigating many points within a short period of time, it is possible, e.g., to scan different polar angles one after each other.

One problem in the measurement of ear canals is that their inner surface is not particularly well suited for optical measurements. One way to increase reflectivity and surface scattering and to reduce volume scattering is to cover the inner surface of the ear canal with talcum powder.

Another possibility comprises to cover the surface to be investigated with a thin deformable layer before the actual measurements take place. The material of said layer is preferably chosen such that an optically optimized surface is formed. The layer has to have a known thickness, should not to deform the topology of the hollow and should fit tightly to the shape of the surface to be investigated. Sensitive areas like the tympanic membrane should not be touched by the layer. In order to achieve a tight fit of the layer to the surface to be measured, a small overpressure in a volume within the layer can be applied, e.g., using a pressure tank or a pump. In order to prevent an overpressure-buildup at the tympanic membrane and a touching of the tympanic membrane, a rigid endplate confining said volume can be foreseen, which is separated from the tympanic membrane by a plate having an opening, which opening is provided with an expandable elastic membrane.

In one embodiment, an endoscope for visual inspection of the hollow can be integrated in or attached to the probe, which greately simplifies the handling when the probe is manually moved. Commerically available endoscopes may be used for this purpose.

In one embodiment, an anti-collision sensor can be integrated in or attached to the probe, which generates a signal when a part of the probe, in particular its tip, is too close to a part of the ear canal. Such an anti-collision sensor may make use of data, which are anyway produced, e.g., data 8 related to color (cf. FIG. 2) or better to data 40 related to distance to point. It is possible to use a reduced resolution for obtaining data for the anti-collision sensor.

Above, various methods and systems for optical, non-contact measurement of the three-dimensional topology of hollows and area regions about their entrances, specifically of ear canals and/or conchas of an individual, have been shown.

The accordingly obtained geometrical data related to the three dimensional shape are, in a preferred embodiment, used for manufacturing at least a part of a hearing device.

A particularly interesting feature of at least some of the above-discussed methods and systems is, that a circumferential surface of a probe can be investigated by means of a chromatic coded distance measurement technique.

LIST OF REFERENCE SYMBOLS 2 probe, measuring head
3 light source, source of polychromatic light, white light source with optics
4 polychromatic light
5 beam splitter, semi-transparent mirror
6 light deflecting unit, mirror arrangement
7 color analyzing unit, spectrometer, color sensor
8 data related to color
9 housing of entrance optics
10 deflected light beam
11 focus point for blue light
12 in-focus point on surface, focus point for green light
13 focus point for red light
14 inner surface, surface of ear canal
15 surface within field of view
16 housing of chromatic optics
17 surface of entrance of ear canal, surface of concha
18 ear canal, hollow
19 evaluation unit
21 tracing element, marker, locator
22 individual's head
23 tracing element carrier
25 tracking unit
40 data related to location of point and distance to point, distance values, distance value along light beam
41 data related to location of point
42 tracking data
50 reconstructing unit
55 reconstruction data
60 light generator in a parabolic mirror
61 beam expander 62 light trap
90 chromatic optics
91 end of chromatic optics
A axis, optical axis

The invention claimed is:

1. A method for manufacturing a hearing device, the method comprising the steps of:
reconstructing a three-dimensional shape of a surface of at least a portion of at least one of an ear canal or a concha, the reconstructing comprising the steps of:
using a chromatic coded distance measurement technique for determining a multitude of distance values respectively representative of a distance to each point of a multitude of points on said surface, using the chromatic coded distance measurement technique further comprising the steps of:
(a) illuminating said multitude of points by means of polychromatic light emitted from a probe located near or in said at least one of said ear canal or concha;
(b) collecting light reemitted from said surface upon said illumination,
(c) analyzing said collected light with respect to color of said light, and
(d) obtaining said multitude of distance values from said analysis;
tracking at least one of:
a position in space or an orientation in space of said probe;
a position in space or an orientation in space of said at least one of said ear canal or concha; or
a relative position or mutual orientation of said probe and said at least one of said ear canal or concha;
and generating corresponding tracking data and
reconstructing said three-dimensional shape based on said multitude of distance values and said tracking data; and
manufacturing at least a part of said hearing device, based on said reconstruction.

2. The method according to claim 1, further comprising the step of moving said probe relative to said at least one of said canal or concha while carrying out steps (a) and (b).

3. The method according to claim 1, wherein said probe comprises a chromatic optical system, and wherein said polychromatic light emitted from said probe forms at least one focused beam towards one of said multitude of points, said reconstructing further comprising the step of choosing at least one of a position or orientation of said probe such that said focused beam is focused at said point for at least one wavelength of said polychromatic light while the beam is focused at least one of before or after said point for other wavelengths of said polychromatic light.

4. The method according to claim 3, wherein said chromatic optical system comprises entrance optics and chromatic optics having an optical axis, said reconstructing further comprising the steps of:
(k) feeding polychromatic light emitted from a light source to said entrance optics;
(l) forming at least one light beam in said entrance optics;
(m) feeding said at least one light beam from said entrance optics to said chromatic optics
at a distance from said optical axis, and
at an azimuthal and a polar angle with respect to said optical axis,
wherein at least one of said distance, said azimuthal angle and said polar angle is selectable by means of said entrance optics; and
(n) forming said focused beam by means of said chromatic optics.

5. The method according to claim 4, further comprising the steps of:
(p) carrying out step (b) by means of said chromatic optics;
(q) feeding said collected light from said chromatic optics to said entrance optics; and
(r) coupling said collected light out of said entrance optics for carrying out step (c).

6. The method according to claim 4, wherein said chromatic optical system has a field of view, which comprises a substantially 360° continuous or quasi-continuous azimuthal angle with respect to said optical axis and which comprises a continuous or quasi-continuous range of polar angles with respect to said optical axis.

7. The method according to claim 1, wherein step (a) is carried out simultaneously for several of said points.

8. The method according to claim 1, wherein said tracking is carried out by means of an optical tracking system.

9. The method according to claim 1, further comprising the step of carrying out said tracking by means of at least one tracing element attached to said probe and at least one tracing element attached to a head of an individual to whom said at least one of said ear canal or concha belong.

10. The method according to claim 1, further comprising the steps of:
monitoring the distance between said probe and said ear canal; and
generating an alert if said distance is below a prescribable threshold distance or if said distance is assumed to drop below said prescribable threshold distance.

11. The method according to claim 10, wherein said monitoring is an optical monitoring.

12. The method according to claim 10, wherein said probe is of generally oblong shape, generally describing an axis along a long dimension of the probe, wherein said monitored distance extends substantially along said axis.

13. The method according to claim 1, further comprising the step of qualitatively visually inspecting said at least one of said ear canal or said concha by means of an endoscope.

14. The method according to claim 1, wherein said probe is capable of emitting polychromatic light towards said at least one of said ear canal or concha by simultaneously emitting several focused beams having distinctly different focal lengths for distinctly different wavelengths of said polychromatic light.

15. A method for manufacturing a hearing device for an individual's left ear and for said individual's right ear, the method comprising carrying out the method according to claim 1 for said individual's left and right ears.

16. The method according to claim 15, further comprising the step of relating said tracking data obtained for said left ear and said tracking data obtained for said right ear to a common coordinate system.

* * * * *